United States Patent [19]
Feinstein et al.

[11] 3,976,665
[45] Aug. 24, 1976

[54] 1,3-ADAMANTYLENE-BIS-TRIMELLITATE DIANHYDRIDES

[75] Inventors: Allen Feinstein, Wheaton; Ellis K. Fields, River Forest, both of Ill.

[73] Assignee: Standard Oil Company (Indiana), Chicago, Ill.

[22] Filed: July 21, 1975

[21] Appl. No.: 597,339

[52] U.S. Cl............................ 260/346.3; 260/78 S; 260/78 TF
[51] Int. Cl.²........................................ C07D 307/89
[58] Field of Search................................. 260/346.3

[56] References Cited
OTHER PUBLICATIONS
Schneider Chem. Abstracts, vol. 68, (1968), 68536p.

Primary Examiner—Henry R. Jiles
Assistant Examiner—Bernard Dentz
Attorney, Agent, or Firm—Gregory E. Croft; Arthur G. Gilkes; William T. McClain

[57] ABSTRACT

Novel dianhydrides derived from trimellitic anhydride and adamantane diacetates are polymerized with a diamine to produce the corresponding polyamide, which is subsequently converted to the polyesterimide by heat treatment at temperatures above 500°F.

2 Claims, No Drawings

1,3-ADAMANTYLENE-BIS-TRIMELLITATE DIANHYDRIDES

BACKGROUND OF THE INVENTION

1. Field of the Invention

This invention relates to polyimides and their precursors. More specifically, this invention relates to polyimides, polyamides, and dianhydrides derived from trimellitic anhydride and adamantane diacetates.

2. Description of the Prior Art

A first patent issued to D. F. Loncrini, U.S. Pat. No. 3,182,073 (1965) discloses the preparation of polyanhydrides of the general formula

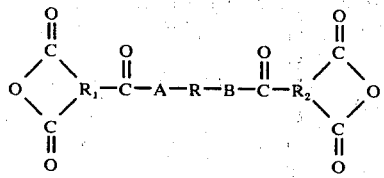

in which A and B can be oxygen, $R_1$ and $R_2$ can be phenyl radicals, and R can be an alicyclic radical such as the divalent radical derived from cyclohexane, cyclobutane, cyclopentane, and the like.

A second patent also issued to Loncrini, U.S. Pat. No. 3,355,427 (1967), which incorporates the '073 patent by reference, discloses the preparation of polyamides and polyimides from diamines and the polyanhydrides disclosed in the '073 patent. Reference is broadly made to the use of alicyclic compounds mentioned in the '073 patent.

However, neither patent contains an enabling disclosure where an alicyclic compound is used to produce a dianhydride, a polyamide, or a polyesterimide. More specifically, the use of an adamantane derivative is not suggested. In fact, those alicyclic compounds which are cited as exemplary are all monocyclic compounds of the same homologous series and are structurally dissimilar to the adamantane derivatives. Because the geometry of the adamantane nucleus will not allow the formation of a double bond between the α and β carbon atoms, adamantane derivatives are unique in that they cannot undergo ester pyrolysis which can readily occur with other alicyclic nuclei such as cyclohexane. This fact coupled with the marked structural difference between Applicant's compositions and those of the prior art are believed to give rise to desirable physical properties such as high heat stability. The polyesterimides are particularly useful for making films, coatings, and molded forms for use at elevated temperatures.

Accordingly, it is an object of this invention to produce a polyesterimide incorporating the adamantane nucleus which is useful for making films, coatings and molded forms for use at elevated temperatures.

It is a further object of this invention to produce a polyamide acid incorporating the adamantane nucleus which is useful in preparing temperature resistant polyesterimides.

It is a further object of this invention to produce a dianhydride incorporating the adamantane nucleus which is useful in preparing temperature resistant polyesterimides.

SUMMARY OF THE INVENTION

In one aspect, the invention resides in a new and useful dianhydride having the general formula

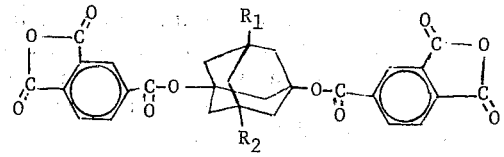

wherein $R_1$ and $R_2$ are individually selected from the group consisting of hydrogen, an alkyl radical, and an aryl radical. Groups $R_1$ and $R_2$ can be the same or different.

In a further aspect, the invention resides in a new and useful polyamide acid formed by reacting the above-mentioned dianhydride with a diamine, said diamine having the general formula

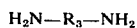

wherein $R_3$ is selected from the group consisting of alkyl, aryl, or heterocyclic radicals.

In a further aspect, the invention resides in a new and useful polyesterimide formed by reacting the above-mentioned dianhydride with the above-mentioned diamine and heating the reaction product to a temperature of at least 500°F.

DESCRIPTION OF THE PREFERRED EMBODIMENT

We have found that the diacetate of adamantane having the general formula

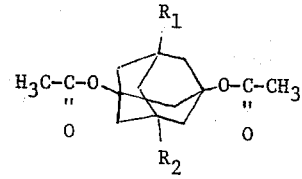

reacts with trimellitic anhydride under the conditions of the transacidolysis reaction described by Hirsch et al. in U.S. 3,183,248 (1965) to give the corresponding dianhydride. $R_1$ and $R_2$ can be hydrogen, alkyl groups, aryl groups such as methyl, ethyl, isopropyl, n-propyl, t-butyl, phenyl, biphenyl, or naphthyl groups. The dianhydride can then by polymerized with a diamine of the general formula

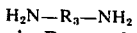

wherein $R_3$ can be aryl, alkyl, or heterocyclic radicals. The resultant polyamide acid can then be subsequently converted to the polyesterimide by heat treatment at temperatures above 500°F., preferably between 500° to 700°F.

EXAMPLE

A solution of 3.87 grams of 1,3-dihydroxyadamantane diacetate and 5.57 grams of trimellitic anhydride was heated at 200°–235°C for 4 hours. The acetic acid generated in the reaction (1.7 grams) was continuously distilled as the reaction proceeded. The reaction mixture was then dissolved in benzene and filtered. The filtrate afforded 3.5 grams of yellow crystals upon being concentrated. A benzene solution of the crystals was heated with charcoal followed by three recrystallizations to yield 1.8 grams of 1,3-adamantylene-bis-trimellitate dianhydride. The anhydride had an uncorrected melting point of 192°–193°C.

A stirred solution of 0.58 grams 4,4'-diaminodiphenyl ether in 9.6 grams N-methyl pyrrolidone was prepared, to which 1.5 grams of the above-mentioned dianhydride was slowly added over a period of 15 minutes. The reaction mixture was stirred for one hour to produce the polyamide acid. The resulting solution had a Gardner Viscosity of 5.5 strokes.

A film cast from the polyamide solution and heated at 600°F for 5 minutes yielded a thermally stable flexible polyesterimide, which, after curing at 300°C. for 16 hours, had a glass transition temperature of 235°C. and did not begin to decompose during thermal gravimetric analysis until heated beyond 390°C.

It will be obvious to those skilled in the art that many variations of the preferred embodiment may be made without departing from the scope of this invention.

We claim:

1. A composition of matter having the general formula

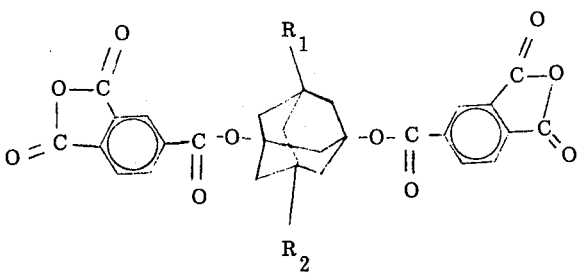

wherein $R_1$ and $R_2$ are radicals individually selected from the group consisting of hydrogen, methyl, ethyl, isopropyl, n-propyl, t-butyl, phenyl, biphenyl, and naphthyl.

2. As a composition of matter, 1,3-adamantylene-bis-trimellitate dianhydride.

* * * * *